US00PP26912P3

(12) United States Plant Patent
Suphachadiwong

(10) Patent No.: US PP26,912 P3
(45) Date of Patent: Jul. 5, 2016

(54) *SANSEVIERIA×DRACAENA* PLANT NAMED 'SUDRASAN01'

(50) Latin Name: *Sansevieria parva×Dracaena godseffiana*
Varietal Denomination: SUDRASAN01

(71) Applicant: Thumrong Suphachadiwong, Bangphra (TH)

(72) Inventor: Thumrong Suphachadiwong, Bangphra (TH)

(73) Assignee: Suphachatwong Innovation (TH)

( * ) Notice: Subject to any disclaimer, the term of this patent is extended or adjusted under 35 U.S.C. 154(b) by 238 days.

(21) Appl. No.: 13/998,815

(22) Filed: Dec. 9, 2013

(65) Prior Publication Data

US 2015/0163986 P1 Jun. 11, 2015

(51) Int. Cl.
*A01H 5/00* (2006.01)

(52) U.S. Cl.
USPC ..... Plt./373; Plt./383; Plt./382

(58) Field of Classification Search
USPC ..... Plt./373, 382, 383
See application file for complete search history.

(56) References Cited

PUBLICATIONS

Europa gazette 2015. www.cpvo.europa.eu/documents/gazettes/2015/cpvo_2015_1.pdf (2 pages).*
UPOV PLUTO: Plant variety database. www3.wipo.int/pluto/user/en/index.jsp (1 page).*

* cited by examiner

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Sansevieria parva×Dracaena godseffiana* cultivar named 'SUDRASAN01' is disclosed, characterized by unique foliage texture, colorations and shape, very short internodes, and highly compact plant form with dense foliage. The new variety is a *Sansevieria×Dracaena*, typically produced as an indoor ornamental plant.

1 Drawing Sheet

Latin name of the genus and species: *Sansevieria parva× Dracaena godseffiana.*

Variety denomination: 'SUDRASAN01'.

BACKGROUND OF THE INVENTION

This application relates to a new cultivar of *Sansevieria parva×Dracaena godseffiana*. The new variety is the product of a planned breeding program. The new variety originated as a seedling from the open pollination of the unpatented, unnamed, proprietary seed parent *Sansevieria parva* with an unidentified, unpatented, proprietary pollen parent *Dracaena godseffiana*. The specific pollen variety is unconfirmed as the cross was made by means of an open pollination process in a nursery where several hybrids of *Dracaena godseffiana* were present. One of multiple proprietary, unnamed, unpatented *Dracaena godseffiana* hybrids could be the pollen parent. These aforementioned *Dracaena godseffiana* hybrids were created by the breeder and never commercially introduced or published and therefore do not have variety names. The cross resulting in 'SUDRASAN01' took place during October of 2003.

The new variety was first observed by the inventor, Thumrong Suphachadiwong, a citizen of Thailand, in 2005 as a seedling, resulting from the above crossing and subsequent planting of seed during 2004, in a research greenhouse belonging to the inventor in Chonburi, Thailand. After identifying the new variety as a potentially interesting selection, the inventor continued confidential testing and propagation of 'SUDRASAN01', assessing stability of the unique characteristics of this variety.

Asexual reproduction of the new cultivar 'SUDRASAN01' was first performed at a research greenhouse belonging to the inventor in Chonburi, Thailand by tip cuttings in 2005. Access to all plants was restricted, as plants were kept in a greenhouse belonging to the inventor, and not accessible to the public. Through subsequent propagation, more than 8 generations have been reproduced, which have shown that the unique features of this cultivar are stable and reproduced true to type.

SUMMARY OF THE INVENTION

The cultivar 'SUDRASAN01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUDRASAN01.' These characteristics in combination distinguish 'SUDRASAN01' as a new and distinct *Sansevieria× Dracaena* cultivar:

1. Very heavy branching from the base.
2. Many side shoots from the base.
3. Produces many leaves and has very short internodes unlike any *Dracaena godseffiana* variety.
4. Compact grow habit, unlike other *Dracaena godseffiana* variety.
5. Unique leaf texture unlike that of any *Dracaena godseffiana* variety, leathery but not tough as leaves of *Sansevieria parva* varieties.

6. Unique small yellow-golden spots on leaf.
7. The growth habit is unique as a whole.

PARENT COMPARISON

Plants of the new cultivar 'SUDRASAN01' are similar to the seed parent, unpatented, unnamed, proprietary *Sansevieria parva* in most horticultural characteristics. However the new variety, 'SUDRASAN01' differs from seed parent in the following characteristics:

1. More heavily branched.
2. Leaves that are longer and not as thick or fleshy.
3. Bushier growth form.

Plants of the new cultivar 'SUDRASAN01' are similar to the potential but unconfirmed pollen parents, *Dracaena godseffiana* in most horticultural characteristics. However the new variety, 'SUDRASAN01' differs from potential pollen parents in the following characteristics:

1. Heavier branching and much shorter internodes.
2. Far more compact plant form.
3. Golden yellow spots on leaves. Potential pollen parents have variegated leaves with many small lemon-yellow areas.
4. Long slim pointy leaves compared to short oval leaves of potential pollen parents.

COMMERCIAL COMPARISON

To the best of the inventor's knowledge, there is no similar *Sansevieria parva×Dracaena godseffiana* variety, however, 'SUDRASAN01' could perhaps be best compared with the unpatented commercial variety *Dracaena godseffiana* 'Milky Way' due to the somewhat similar spotting of the foliage. However the new variety, 'SUDRASAN01' differs from 'Milky Way' in the following characteristics:

1. Foliage of the new variety has more spotted variegation, of a different color.
2. Heavier branching and much shorter internodes.
3. Far more compact plant form.
4. Long slim pointy leaves compared to short oval leaves of 'Milky Way'.

BRIEF DESCRIPTION OF THE PHOTOGRAPH

The accompanying photograph in FIG. 1 illustrates in full color a typical plant of 'SUDRASAN01' grown in a commercial greenhouse in Honselersdijk, the Netherlands. The plant is 40 weeks old in a 17 cm circular pot.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SUDRASAN01' plant bred in Chonburi, Thailand and hardened in a commercial greenhouse in Honselersdijk, the Netherlands. The plant is 40 weeks old in a 17 cm circular pot. Low temperature was approximately 18° C. high temperature was approximately 26° C. No photoperiodic or chemical treatments were given to the plants. Measurements and numerical values represent averages of typical plant types.

Botanical classification: *Sansevieria parva×Dracaena godseffiana* 'SUDRASAN01'.

PROPAGATION

Time to initiate rooting: About 4 weeks at approximately 18° to 26° C.

Root description: Not very thick, slightly fibrous, not fleshy, young roots orange-white, near RHS 159A, older roots greyed-orange, near RHS N167B.

PLANT

Growth habit: Broad upright.
Height: Approximately 41.0 cm.
Plant spread: Approximately 52.0 cm.
Growth rate: Moderate, approximately 10 cm per month.
Branching characteristics: Basal branching, moderately free; average number of lateral stems: 7.
Diameter of stem: Approximately 0.6 cm.
Internode length: Average 0.5 cm.
Texture of stem: Smooth, matte.
Color of stem: Yellow-green, near RHS 152A and 150D, older stems brown; near RHS N200A.
Stem strength: Very strong.
Number of leaves per stem: Average 24.

FOLIAGE

Leaf:

*Arrangement*.—Alternate (spirally).
*Average length*.—Approximately 24.2 cm (including sheath).
*Average width*.—Approximately 2.5 cm.
*Shape of blade*.—Narrow lorate, carinate.
*Aspect*.—Leaves in an average angle of 40° to stem.
*Apex*.—Pungent; not sharp to the touch.
*Base*.—Cuneate.
*Attachment*.—Sheathing.
*Margin*.—Entire, moderately undulate.
*Texture of top surface*.—Smooth, moderately glossy.
*Texture of bottom surface*.—Smooth, moderately glossy.
*Color*.—Young foliage upper side: Green to yellow-green; near RHS 143A and 144A, irregularly dotted yellow-green; near RHS 150B and 150C. Young foliage under side: Green; near RHS 143C, tip darker; near RHS 143A, irregularly dotted yellow-green; near RHS 145B. Mature foliage upper side: Green to yellow-green; in between near RHS N137A to 147A but considerably darker, irregularly dotted yellow-green; near RHS 150C. Mature foliage under side: Green; in between near RHS 137B and 143A, irregularly dotted yellow-green; near RHS 150B.
*Venation*.—Type: Parallel. Color: Upperside: As leaf blade. Underside: As leaf blade.

Sheath:

*Average length*.—Approximately 0.5 cm.
*Average width*.—Approximately 0.8 cm.
*Color*.—Yellow-green; near RHS 145D.
*Texture*.—Smooth, moderately glossy.

*Other distinguishing characteristics*.—Leaves relatively thick (approximately 1 mm) and moderately leathery.

OTHER CHARACTERISTICS

Flowering: Not observed to date.

Disease resistance: Neither resistance nor susceptibility to the normal diseases found in *Sansevieria* or *Dracaena* has been observed.

Drought tolerance and cold tolerance: Moderately high drought resistance, good heat resistance.

Fruit/seed production: No fruits/seeds detected to date.

What is claimed is:

1. A new and distinct cultivar of *Sansevieria parva*×*Dracaena godseffiana* plant named 'SUDRASAN01' as herein illustrated and described.

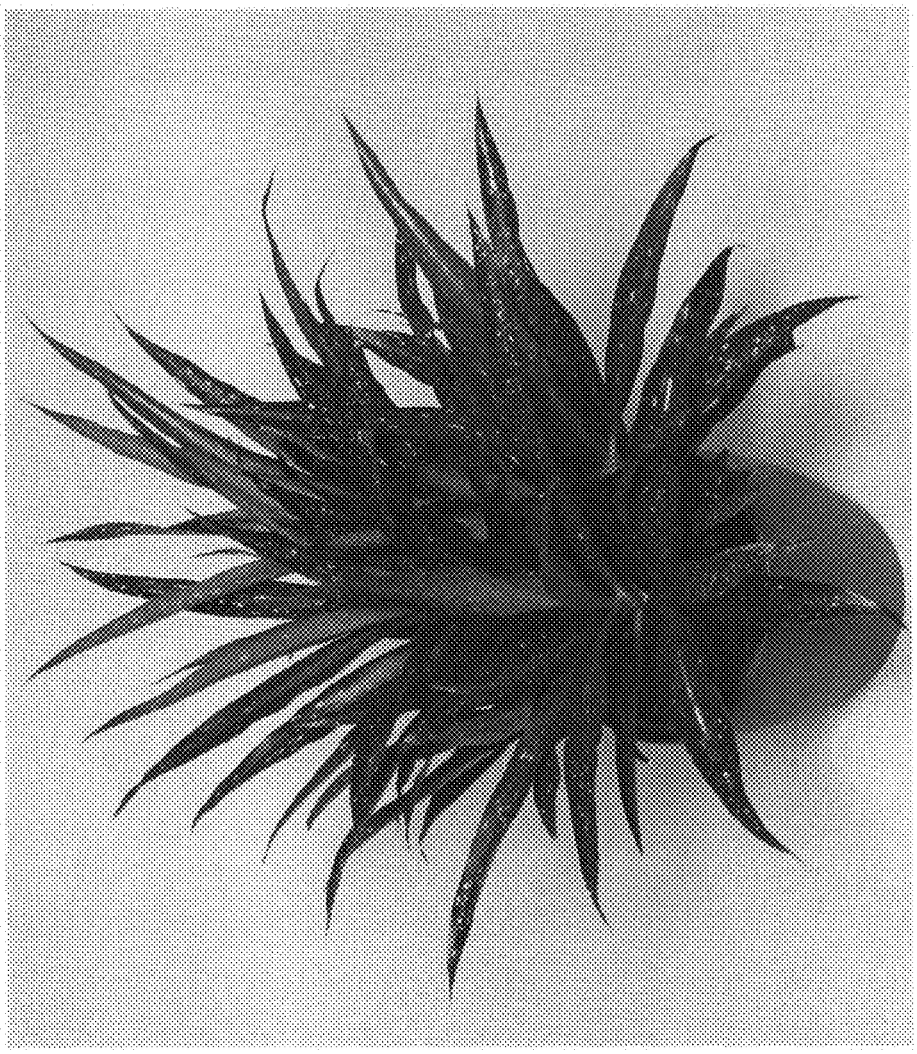

* * * * *